United States Patent [19]

Stanley et al.

[11] 4,077,390
[45] Mar. 7, 1978

[54] REUSABLE HEAT PACK CONTAINING SUPERCOOLED SOLUTION AND MEANS FOR ACTIVATING SAME

[75] Inventors: Joseph Stanley, Topanga; Griffith L. Hoerner, Santa Monica, both of Calif.

[73] Assignees: Marc F. Fiedler, Sherman Oaks; Herman Siegel, Los Angeles, both of Calif.

[21] Appl. No.: 710,394

[22] Filed: Aug. 2, 1976

[51] Int. Cl.² .............................................. F24J 1/00
[52] U.S. Cl. ......................................... 126/263; 62/4; 23/301; 126/400; 165/DIG. 4
[58] Field of Search .................. 62/4; 126/263, 400; 44/3 R, 3 A, 3 B, 3 C; 165/DIG. 4, 104 S; 23/300, 301 R; 156/621; 252/71

[56] References Cited

U.S. PATENT DOCUMENTS

| 1,384,747 | 7/1921 | Eckelmann et al. | 126/263 |
| 1,385,074 | 7/1921 | Ferguson | 126/263 |
| 1,920,853 | 8/1933 | Ferguson | 126/263 |
| 2,220,777 | 11/1940 | Othmer | 126/263 |
| 2,386,654 | 10/1945 | Caldwell | 126/263 |

Primary Examiner—Ronald C. Capossela

[57] ABSTRACT

A heat pack is made by enclosing supercoolable aqueous sodium acetate solution together with a metallic activator strip in a sealed, flexible container. The activator strip is a flexible metal strip having one or more fissures or slits extending therethrough.

To prepare the heat pack for activation, its contents are first heated to a temperature above the melting point of sodium acetate to completely melt it. Thereafter, the sodium acetate solution is supercooled. Activation or crystallization of the sodium acetate (with evolution of heat) is produced by bending the activator strip.

12 Claims, 7 Drawing Figures

U.S. Patent    March 7, 1978    4,077,390
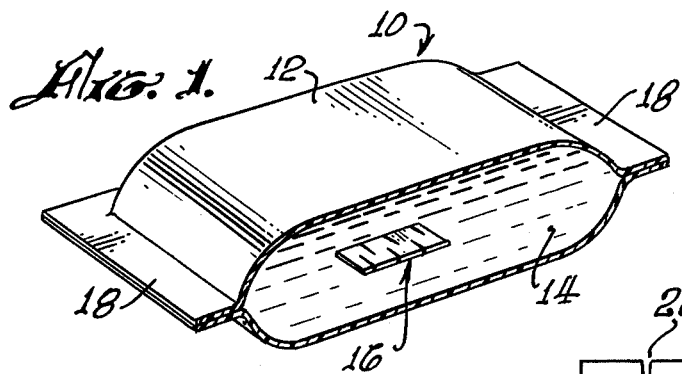
FIG. 1.
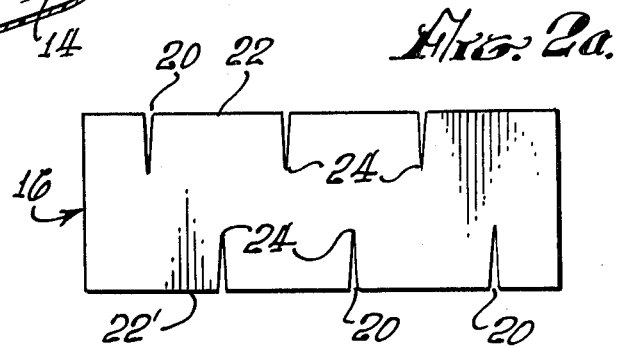
FIG. 2a.
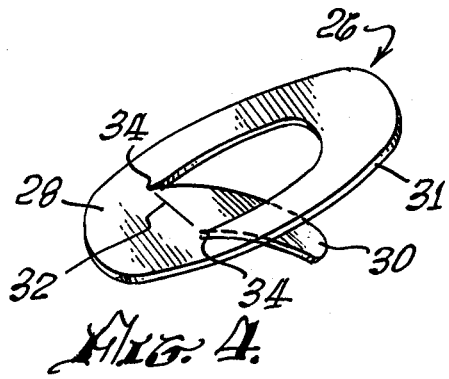
FIG. 4.
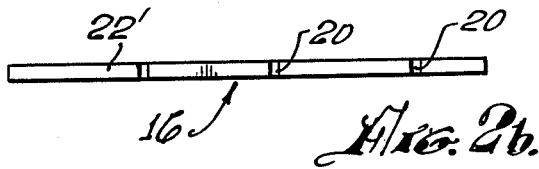
FIG. 2b.
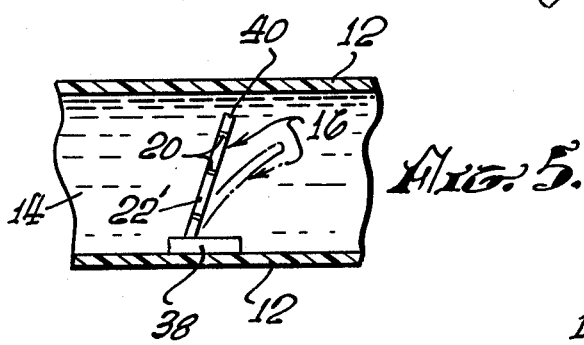
FIG. 3.
FIG. 5.
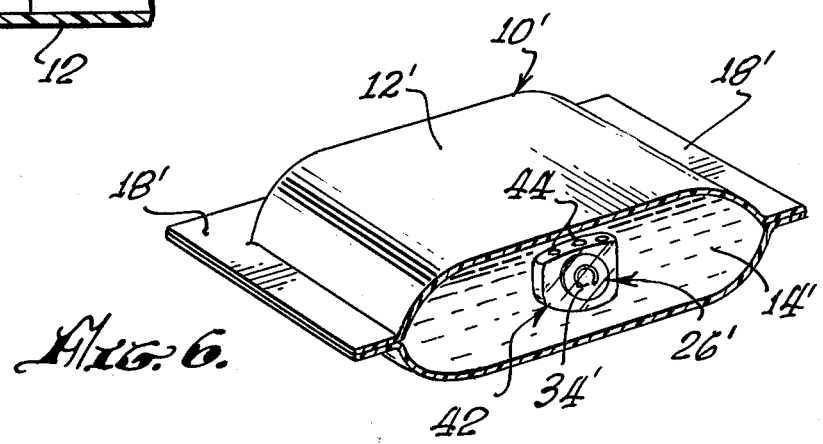
FIG. 6.

REUSABLE HEAT PACK CONTAINING SUPERCOOLED SOLUTION AND MEANS FOR ACTIVATING SAME

BACKGROUND OF THE INVENTION

The invention relates to reusable heat packs and, more particularly, to heat packs containing supercooled solutions which liberate heat when caused to crystallize.

Heat packs of various types have long been used in the medical field and by sportsmen for the purpose of applying heat to localized areas of the body to, for example, alleviate stiffness and minimize damage due to freezing of the skin. The simplest form of a heat pack is a hot water bottle. Although water has a high heat content, the temperature of the water is difficult to control for any length of time and heating of the water may be impossible when most needed, as when the need arises to treat frozen appendages in the field.

To provide improved heat sources, heat packs have been developed using aqueous salt solutions which can be supercooled so that the heat packs can be carried in the supercooled condition and activated with internal release of heat when desired. Sodium acetate and calcium nitrate tetrahydrate are examples of suitable salts.

With respect to the use of supercooled sodium acetate solutions in heat packs, activation or crystallization initiation has presented a problem. Various techniques have been recommended including: contacting some of the supercooled solution with air; inserting a crystal of material into the supercooled solution; and scraping the inside of a container made from a hard material such as metal with a wire to introduced impurities into the supercooled solution. Examples of these techniques are disclosed in the following U.S. Pat. Nos. 1,433,010; 1,915,523; 2,289,425; 2,220,777; and 3,093,308. The existence of many such patents over a long time period is indicative of the continuing need for a simple, effective means for activating supercooled aqueous sodium acetate solutions so that more versatile heat packs can be developed using such solutions.

Aforementioned U.S. Pat. No. 2,220,777 discloses a self-contained heater which, in one embodiment shown in FIG. 12 thereof, may be flexible, but which requires at least two metallic components which must be scraped together by a user in order to activate a supercooled solution contained therein. The need to use at least two metallic components and the necessity of scraping them together can place undesired restrictions on the design of the heater. For example, heat loss will be greater as the number of metallic components increases or it will be more expensive to insulate the heater against such heat loss. Additionally, heater size and/or its fluid content will be limited because of the need to be able to bring the two metallic components together.

SUMMARY OF THE INVENTION

An aqueous sodium acetate solution and a herein-described activator strip comprising a flexible ferrous metal strip weakened by one or more fissures or slits are introduced into a flexible container which is then sealed. The container and its contents are thereafter heated to a temperature above the melting point of the sodium acetate to completely liquify it. After this is acomplished, the container contents are supercooled.

The supercooled sodium acetate solution is activated by flexing or bending the activator strip. Sodium acetate crystals are thereby produced and heat is evolved. Reuse of the heat pack is effected by merely sequentially reheating and supercooling the container contents.

Besides being of simple construction and operation, the herein-described heat pack eliminates the need to anchor or install an activating device to or on the container walls thereby greatly reducing the cost of manufacturing the container. Additionally, because the activator is self-contained, i.e., it does not act in combination with the container walls to produce crystallization as by scraping, as described in U.S. Pat. No. 2,220,777, the container can be made from relatively thin plastic materials which, because of their flexibility, permit the heat pack to conform to the contours of a user's body. Furthermore, the herein-described activator strip can be reused countless times without removal from a sealed heat pack.

DESCRIPTION OF THE DRAWINGS

FIG. 1 is a perspective, sectional view of the herein-described heat pack.

FIGS. 2a and 2b are a plan view and a side edge view, respectively, of one embodiment of the activator strip which may be used in the heat pack of FIG. 1.

FIG. 3 is a side elevational view of the activator strip of FIG. 2 illustrating its use.

FIG. 4 is a perspective view of another embodiment of the herein-described activator strip.

FIG. 5 is a sectional elevational view of a heat pack of this invention showing a method of fixedly locating the activator strip within the heat pack.

FIG. 6 is a sectioned, perspective view of a heat pack showing protective means for preventing the heat pack from being cut by the activator strip within the heat pack.

DESCRIPTION OF THE PREFERRED EMBODIMENT

In brief, an improvement is made in heat packs containing aqueous sodium acetate solution. That improvement is embodied in a flexible activator strip which is disposed within the heat pack in intimate contact with the sodium acetate solution. When flexed or bent, the activator strip causes the sodium acetate solution when supercooled to crystalize with ensuing evolution of heat.

More specifically, and with reference first to FIG. 1, the numeral 10 designates the herein-described heat pack which comprises a flexible container 12, an aqueous sodium acetate solution 14, and an activator strip 16. The container 12 is made from a flexible material which is not affected by the sodium acetate solution and which is impermeable to the sodium acetate solution. Additionally, the container material must be able to withstand the temperatures (generally on the order of about 60°–65° C.) to which the heat pack 10 is heated to melt the solidified sodium acetate solution 14 after the heat pack has been used prior to re-use. Preferably, the material forming the container 12 is clear so that the activator strip 16 can be easily seen. Suitable materials include plastic materials such as rubber, vinyl, vinyl-coated fabric and polyethylene. A thickness of about 0.005 in. (0.13 mm.) has been found to be satisfactory using clear vinyl. Initially, the container 12 has an open end or side for introduction of the sodium acetate solution 14 and activator strip 16, whereas the other sides or edges 18 may be heat sealed. After addition of the sodium acetate solution to the heat pack 10, the open side is sealed to make the heat pack fluid-tight. The size and shape of the heat pack 10 will vary according to its use.

The sodium acetate solution 14 is made by dissolving sodium acetate in the desired amount of water. The amount of sodium acetate utilized should permit the sodium acetate solution to be supercooled to at least the ambient temperature at which the heat pack is intended to be utilized. Additionally, the amount of sodium acetate should not be so great that the resulting solution is activated unintentionally by shaking, etc., when at ambient or use temperature. For example, if a heat pack is to be utilized at 0° C., then the amount of sodium acetate used should permit supercooling of the sodium acetate solution down to at least that temperature and the solution should be relatively stable at that temperature. However, sufficient sodium acetate should be used to enable the supercooled solution to be readily crystallized when the activator strip 16 is flexed.

The amount of water present in the sodium acetate solution will vary depending upon the heat pack temperature desired (assuming that the amount or concentration of sodium acetate present satisfies the aforementioned criteria of use at ambient temperature and ease of crystallization). As the amount of water increases relative to the amount of sodium acetate, the temperature to which the container contents are raised when the sodium acetate crystallizes decreases. This means that the maximum temperature of the heat pack 10 can be controlled by appropriate adjustment of the water/sodium acetate ratio for any effective amount (as described hereinbefore) of sodium acetate.

Hereinbefore, there has been described a sodium acetate heat pack, the construction of which is known. To that extent, it does not constitute an essential part of the herein-described invention except to the extent that it provides a supercoolable vehicle for activation by the activator strip to be described hereinafter.

In general, the activator strip is a flexible strip made from a ferrous material such as metal, and preferably stainless steel.

The activator strip is provided with at least one, and preferably, a plurality of fissures or slits extending thereinto in a thickness direction. As will be further described hereinafter, the fissues can extend inwardly from the edges or perimeter of the strip or they can be located intermediate the edges or perimeter of the strip.

Turning again to FIG. 1 and to FIG. 2a and 2b, one embodiment 16 of the herein-described activator strip is shown in these Figures. That embodiment 16 has a plurality of fissures 20 extending inwardly from juxtaposed side edges 22, 22′ a partial distance toward the other of the side edges so that the fissures taper to, and terminate in, blind ends terminii 24 within the strip. The fissures 20 need not be disposed in any particular pattern and they need not extend inwardly from more than one edge. As flexing of the activator strip 16 occurs, crystals of sodium acetate are initially produced at the blind ends 24 of one or more of the fissures 20. These initial crystals, in turn, cause crystal propagation throughout the sodium acetate solution as is well known.

Activation of a supercooled sodium acetate solution is effected by flexing or bending the activator strip. This is done by grasping the activator strip through the container material and bending it as shown by way of illustration in FIG. 3. As flexing of the activator strip 16 occurs, crystals of sodium acetate are initially produced at the blind ends 24 of one or more of the fissures 20. These initial crystals, in turn, cause crystal propagation throughout the sodium acetate solution as is well known.

It is not presently fully understood how the activator strip 16 initiates crystallization of the supercooled sodium acetate solution; however, it is believed that flexing produces minute continuances or extensions of fracturing at the blind ends 24 of the fissures 20 and that these new fractures are instrumental in initiating crystallization. If this belief is correct, these extensions are extremely small since an activator strip can be used hundreds of times without breaking.

A second embodiment of the herein-described activator strip is shown in FIG. 4 in which the numeral 26 represents an activator strip having a body portion 28 and a tongue 30 depending therefrom interiorly of the edges 31 thereof. The tongue 30 is integrally attached at its rearward end 32 to the body 28 from which it is formed by, for example, stamping. A pair of fissures 34,34 are defined by confronting surfaces of the tongue 30 and body 28.

Activation of a supercooled solution by the activator strip 26 is effected by flexing the tongue 30 relative to the body 28 by bending the former about its rearward end 32 toward and away from the body portion 28.

An activator strip may be permanently located at a specific location in a heat pack by anchoring it at a particular position against an inner surface of the latter as exemplified by FIG. 5. As shown in FIG. 5, the activator strip 16 (or the embodiment 26) is bonded at one end to the interior of the flexible container 12 using an adhesive button 38 made from, for example, an epoxy resin which will not adversely affect the sodium acetate solution. The other or free end 40 of the activator strip 26 projects into the sodium acetate solution 14. Activation again is effected by flexing the activator strip 16 as previously described (except that one end of the latter is fixed) after the sodium acetate solution 14 has been supercooled.

Turning now to FIG. 6, there is shown in that Figure another means for locating an activator strip at a particular position within a heat pack. In addition, the FIG. 6 embodiment has the added advantage of preventing a flexible container from being cut by an activator strip.

In FIG. 6, the numeral 10′ designates a heat pack which may be the same as that shown in FIG. 1. The heat pack 10′ comprises a flexible container 12′ containing sodium acetate solution 14′. Disposed interiorly of the flexible container 12′ and preferably (but not necessarily) bonded thereto utilizing an adhesive or by heat sealing is a second and smaller flexible container or bag 42 referred to as a protective bag. An activator strip 26′ as shown (or the embodiment 16) is disposed within the protective bag 42.

The protective bag 42 may be made in the same manner and from the same materials as the larger flexible container 12′. However, it must be provided with at least one and, preferably, a plurality of apertures 44 extending through its walls to provide communication between the interior and exterior of the protective bag 42, i.e., between the interior of the protective bag 42 and the interior of the outer flexible container 12′. Such communication ensures that the protective bag 42 will be filled with sodium acetate solution 14′. When the latter is activated within the protective bag 42 by bending the activator strip 26′, sodium acetate crystals thereby formed will be able to spread (grow) through the apertures 44 into the sodium acetate solution 14' external to the protective bag 42.

The invention will now be further described by the following Examples.

EXAMPLE 1

Into a vinyl (polyvinyl alcohol) bag sealed along three sides, there were introduced 100 grams of anhydrous sodium acetate, 100 grams of water (tap), and a stainless steel activator strip. The latter had one shear cut extending inwardly from one side, near the center. The activator strip dimensions were 2.54 cm. × 1.9 cm. × 0.16 cm. The cut was 0.63 cm. in length.

The fourth side of the bag was then sealed, and the bag was placed in boiling water in order to heat the contents to a temperature in excess of 60.0° C to ensure complete melting of the sodium acetate solution. Thereafter, the bag was supercooled to room temperature.

The activator strip was flexed whereupon crystals began forming in the supercooled solution, initially adjacent to the edge cut. Heat was evolved and the temperature of the pack rose to about 38° C.

The foregoing heating and cooling steps followed by crystallization were repeated several times with the same results.

EXAMPLE 2

Example 1 was repeated except that the amount of water was reduced from 100 grams to 50 grams.

The temperature produced after activation was about 57° C.

EXAMPLE 3

Example 1 was repeated except that only 75 grams of water were used.

The temperature produced after activation was about 54° C.

Example 1 has been repeated with similar results using activator strips having a plurality of edge fissures as shown in FIG. 1 and using an activator strip having a flexible tongue as shown in FIG. 4.

There has been described an activator strip which, when flexed, causes crystallization of a supercooled aqueous sodium acetate solution with the evolution of heat. The activator strip is characterized in that it defines or has formed therein fissures extending therethrough in a thickness direction. Variations from the specific embodiments of the activator strip which have been described herein may be made without departing from the spirit of the invention as will be understood by those skilled in the art. For example, the annular ring formed by the body portion 28 need not be continuous as shown in FIG. 4. Instead, it may be discontinuous with the tongue being longer than that shown in FIG. 4 by the width of the ring, but still depending from a finite or limited region of the inner surface of the annular ring as in FIG. 4.

We claim:

1. A heat pack comprising:
a flexible container;
a supercoolable aqueous sodium acetate solution carried within said flexible container; and
a flexible self contained activator strip disposed within said flexible container in intimate contact with said sodium acetate solution for initiating crystallization of said solution when supercooled, said activator strip having no dependency with said flexible container for said crystallization, said activator strip being formed from a ferrous material defining a thickness and a perimeter and including at least one fissure extending through said thickness and having a terminus inwardly of said perimeter.

2. The heat pack of claim 1 wherein said at least one fissure extends inwardly from the perimeter of said activator strip.

3. The heat pack of claim 1 wherein said self contained activator strip comprises a body portion and a tongue portion integrally attached at one end thereof to said body portion and depending therefrom intermediate the perimeter of said activator strip, confronting surfaces of said body and tongue portions defining therebetween said at least one fissure.

4. The heat pack of claim 3 wherein said body portion forms a continuous annular ring with said tongue portion depending from a discrete region along the interior surface of said ring.

5. The heat pack of claim 1 wherein said heat pack further comprises:
a flexible protective bag disposed within said sodium acetate solution and defining at least one aperture extending therethrough for providing fluid communication between the interior of said protective bag and the interior of said flexible container exterior to said self contained protective bag, said activator strip being disposed within said flexible bag whereby flexing of said activator strip initiates crystal formation within said protective bag with said crystals growing therefrom into said flexible container exterior to said protective bag.

6. The heat pack of claim 5 wherein said protective bag is fixedly attached to said flexible container.

7. The heat pack of claim 1 wherein said activator strip is formed from steel.

8. A method of initiating crystallization of a supercoolable aqueous sodium acetate solution carried within a flexible container, said method comprising the steps of
introducing a flexible activator strip into said supercoolable solution, said activator strip being formed from a ferrous material defining a thickness and a perimeter and including at least one fissure extending through said thickness and having a terminus inwardly of said perimeter; and
flexing said activator strip through said flexible container to initiate crystallization of said supercoolable solution wherein said strip has no dependency with said container for crystallization.

9. The method of claim 8 including the additional step of:
sealing said flexible container after introduction of said activator strip into said flexible container and before said flexing of said activator strip.

10. The method of claim 9 including the further sequential steps of:
heating said supercoolable solution to a temperature sufficient to completely melt said supercoolable solution after said sealing of said flexible container; and
said supercoolable solution to a temperature at which said supercoolable solution is supercooled before flexing said activator strip.

11. The method of claim 10 wherein said steps are sequentially repeated to alternately initiate crystallization of, and supercool, said supercoolable solution.

12. A heat pack as defined in claim 1 wherein the flexible container is formed from pliable polymer compatible with said soduim acetate solution and said solution and flexible self contained activator strip are sealed therein.

* * * * *